(12) United States Patent
Kinoshita et al.

(10) Patent No.: US 7,341,579 B2
(45) Date of Patent: Mar. 11, 2008

(54) SANITARY NAPKIN

(75) Inventors: Masataka Kinoshita, Kagawa (JP); Takuya Miyama, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 11/177,220

(22) Filed: Jul. 7, 2005

(65) Prior Publication Data

US 2006/0009747 A1    Jan. 12, 2006

(30) Foreign Application Priority Data

Jul. 9, 2004    (JP) .............................. 2004-202576

(51) Int. Cl.
*A61F 13/15* (2006.01)
(52) U.S. Cl. ........................ 604/385.04; 604/385.05; 604/385.03; 604/386; 604/387
(58) Field of Classification Search ........... 604/385.03, 604/385.04, 358.05, 386, 387
See application file for complete search history.

(56) References Cited

U.S. PATENT DOCUMENTS

| | | | | |
|---|---|---|---|---|
| 4,720,415 A * | 1/1988 | Vander Wielen et al. ... | 428/152 |
| 5,576,090 A * | 11/1996 | Suzuki ........................ | 428/152 |
| 5,873,869 A * | 2/1999 | Hammons et al. ..... | 604/385.01 |
| 5,906,008 A * | 5/1999 | Heki et al. ...................... | 2/400 |
| 6,168,582 B1 * | 1/2001 | Hasegawa .............. | 604/385.02 |
| 6,200,299 B1 * | 3/2001 | Heki .......................... | 604/386 |
| 6,280,428 B1 * | 8/2001 | Lash et al. ............. | 604/385.04 |
| 6,284,943 B1 * | 9/2001 | Osborn et al. .............. | 604/366 |
| 6,328,722 B1 * | 12/2001 | Lavash et al. ......... | 604/385.04 |
| 6,458,112 B1 * | 10/2002 | Marshall et al. ....... | 604/385.04 |
| 6,511,464 B1 * | 1/2003 | Suekane ................ | 604/385.04 |
| 6,569,140 B1 * | 5/2003 | Mizutani et al. ....... | 604/385.28 |
| 6,579,272 B1 * | 6/2003 | Samuelsson et al. .. | 604/385.01 |
| 6,616,644 B1 * | 9/2003 | Mizutani ............... | 604/385.04 |
| 2003/0023221 A1 * | 1/2003 | Kashiwagi et al. .... | 604/385.04 |
| 2004/0068244 A1 * | 4/2004 | Salone et al. .......... | 604/385.04 |

FOREIGN PATENT DOCUMENTS

| | | |
|---|---|---|
| JP | 9-500558 | 1/1997 |
| JP | 2003-339765 | 12/2003 |
| WO | WO-95/03023 | 2/1995 |
| WO | WO 9520931 A1 * | 8/1995 |

OTHER PUBLICATIONS

Machine-assisted translation of Jp 2003-339765 from JPO web database, accessed Oct. 6, 2005.*

* cited by examiner

*Primary Examiner*—Jacqueline F. Stephens
(74) *Attorney, Agent, or Firm*—Darby & Darby P.C.

(57) ABSTRACT

A sanitary napkin includes an elongated main body having a liquid absorbent layer for absorbing and retaining liquid and rear flaps projecting laterally in opposite directions from a rear part of the main body. The sanitary napkin is adapted to be worn with the rear flaps kept in an unfolded state on an inner side of an undergarment. Each rear flap included a first sheet with corrugated regions and a longitudinally-extending strip-shaped or linear smooth region defined between adjacent corrugated regions. Each corrugated region has hills and valleys which extend laterally and alternate with each other longitudinally. The smooth region is free of the hills and valleys or has a smaller difference in level between hills and valleys than the corrugated region.

10 Claims, 8 Drawing Sheets

SANITARY NAPKIN

BACKGROUND OF THE INVENTION

1. Field of the Invention

The present invention relates to a sanitary napkin having a main body capable of absorbing and retaining liquid and rear flaps projecting laterally in opposite directions from a rear part of the main body and more particularly to a sanitary napkin whose rear flaps when worn easily deform in accordance with the body shape of a wearer, feel good to the touch and are resistant to wrinkling.

2. Description of the Related Art

Sanitary napkins have a main body with a liquid absorbent layer interposed between a liquid-permeable topsheet and a liquid-impermeable backsheet. When the main body is applied to the crotch region of a woman, liquids discharged from the vaginal opening can be absorbed by the liquid absorbent layer through the topsheet.

Such sanitary napkins include elongated ones which are designed such that the vaginal opening may face a front part of the main body and the intergluteal cleft (i.e., the furrow of the buttocks), as well as the anus, may be covered with a rear part of the main body. Typically, the elongated sanitary napkins are provided with rear flaps projecting laterally in opposite directions from the rear part of the main body. When a wearer is sleeping on her back or sitting for a long time, for example, menstrual blood tending to migrate posteriorly from the vaginal opening can be absorbed by the rear part of the main body of the sanitary napkin and furthermore menstrual blood tending to flow out laterally from the rear part of the main body can be received by the rear flaps, which prevents an undergarment from being stained.

When the sanitary napkin is worn, the rear flaps, which are kept in an unfolded state and laid on an inner side of an undergarment, come into close contact with the wearer's body. However, if the wearer's legs move during wearing of the sanitary napkin, the body shape will change in the crotch region and the buttocks and therefore the undergarment will be partially stretched or twisted to exert a deforming force on the rear flaps. This results in twisting or wrinkling the rear flaps during wearing of the sanitary napkin.

Japanese Unexamined Patent Publication No. 2003-339765 discloses a sanitary napkin in which stiffness of the rear flap is increased by forming a great number of embossments in a nonwoven fabric used for the rear flap. More specifically, the rear flap is constructed by laying a nonwoven fabric on a body surface of a resin film (backsheet). The rear flap is held between a pattern roll with a given pattern of projections and a roll with a smooth peripheral surface, so that the laminate is locally pressed against the smooth peripheral surface by the projections to have the embossments with increased density. This leads to increasing the stiffness of the rear flap. Patent Publication No. 2003-339765 discloses that the embossments in the rear flap may extend laterally or obliquely in a striped patter or may extend in a lattice pattern.

However, if the stiffness is increased by forming a great number of embossments in the rear flaps as disclosed in Patent Publication No. 2003-339765, the rear flaps, which are kept in an unfolded state on the undergarment, tend to resist deformation in accordance with the wearer's body shape, which may cause an unpleasant feeling. Particularly when the embossments extend laterally in a striped pattern, the rear flaps tend to resist bending in the lateral direction. In addition, the front parts of the rear flaps are typically positioned to face the inner thighs, whose surface shape tends to change as the legs move. Therefore, if the stiffness is increased in the front parts of the rear flaps as disclosed in Patent Publication No. 2003-339765, the front parts tend to resist deformation in accordance with the body shape, which may give an unpleasant feeling to the thighs and result in an uncomfortable fit.

On the other hand, Japanese Unexamined Patent Publication No. H09-500558 discloses a sanitary napkin in which flaps projecting laterally in opposite directions from a main body have first regions where a sheet is corrugated. In the first region, hills and valleys extend linearly and longitudinally. In FIGS. 6 and 7 of Patent Publication No. H09-500558, moreover, the flap is provided not only with the first region but also with a second region which is less expandable and extends laterally.

However, the flaps disclosed in Patent Publication No. H09-500558 are intended to project outwardly from the side edges of the crotch region of an undergarment when the main body is attached to the inner side of the crotch region of the undergarment. The reason for providing the first region in the flap is such that the flaps may be easily folded back against the outer side of the undergarment when the undergarment is pulled up with the main body mounted on the inner side of the crotch region of the undergarment.

That is, the flaps disclosed in Patent Publication No. H09-500558 are not intended to be kept in an unfolded state on the inner side of the undergarment when worn. In addition, the corrugated first region is not aimed at facilitating deformation of the unfolded flaps in accordance with the body shape.

SUMMARY OF THE INVENTION

The present invention has been developed to solve the problems in the prior art set forth above and has an object to provide a sanitary napkin whose rear flaps, which is to be kept in an unfolded state on an inner side of an undergarment for fitting the body of a wearer, can easily deform in accordance with the body shape of a wearer while resisting wrinkling and twisting and avoiding an unpleasant feeling.

According to the present invention, there is provided a sanitary napkin comprising:

an elongated main body having a liquid absorbent layer for absorbing and retaining liquid; and rear flaps projecting laterally in opposite directions from a rear part of the main body, the sanitary napkin being adapted to be worn with the rear flaps kept in an unfolded state on an inner side of an undergarment, each rear flap including a first sheet with corrugated regions and a longitudinally-extending strip-shaped or linear smooth region defined between adjacent corrugated regions, each corrugated region having hills and valleys which extend laterally and alternate with each other longitudinally, the smooth region being free of the hills and valleys or having a smaller difference in level between hills and valleys than the corrugated region.

In the sanitary napkin according to the present invention, since the rear flaps with the corrugated regions are highly flexible in the longitudinal direction and are also allowed to easily bend in the lateral direction at the longitudinally-extending smooth regions, the rear flaps can easily deform in accordance with the body shape of a wearer. Particularly when the corrugated regions and the smooth region are formed in a front part of each rear flap, the rear flaps can easily follow the change in shape of the inner thighs or the undergarment. In addition, the rear flaps with such low bending stiffness hardly give an unpleasant feeling to the wearer's body, particularly at and near the inner thighs that will deform significantly.

Preferably, each rear flap further includes a second sheet laid on a garment surface of the first sheet, wherein the corrugated regions are bonded at bottoms of the valleys to the second sheet or another sheet disposed between the first sheet and the second sheet. With this construction, the corrugated regions may have a high bulk recovery ratio. When the rear flap is concavely bent, moreover, the corrugate regions may deform as shown in FIG. 6(B) without providing high resistance. Therefore, the rear flaps subjected to an external force is resistant to wrinkling and twisting.

The hills and valleys of the corrugated region may be arranged at a fixed pitch or at a finer pitch in a front part of each rear flap than in a rear part behind the front part so that the front part can easily follow the movement of the wearer's body at or near the inner thighs.

The smooth region may extend longitudinally continuously or intermittently.

Preferably, each rear flap has a plurality of smooth regions at laterally spaced intervals. With this construction, the lateral bending stiffness of each rear flap may be decreased to further facilitate deformation in accordance with the body shape.

Preferably, the corrugated region has a bulk recovery ratio in the range of 70% to 90%. Also preferably, the first sheet has a ring crush strength equal to or less than 60% of an original ring crush strength as measured before formation of the corrugated regions and the smooth region.

BRIEF DESCRIPTION OF THE DRAWINGS

The present invention will be understood more fully from the detailed description given hereinafter and from the accompanying drawings of the preferred embodiments of the present invention, which, however, should not be taken to limit the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscuring of the present invention.

Figure 1:
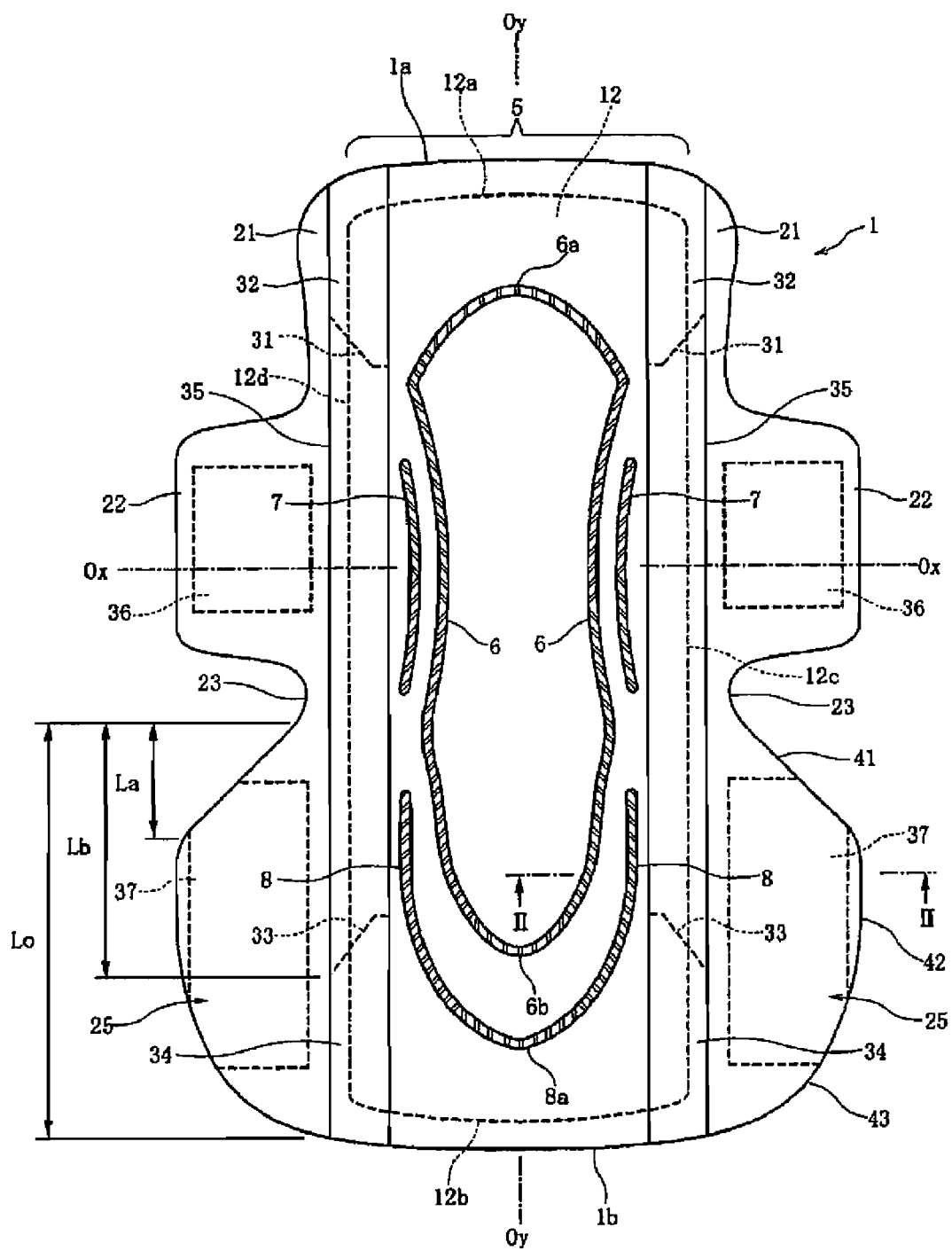
FIG. 1 is a plan view of a sanitary napkin according to one embodiment of the present invention.
Figure 2:
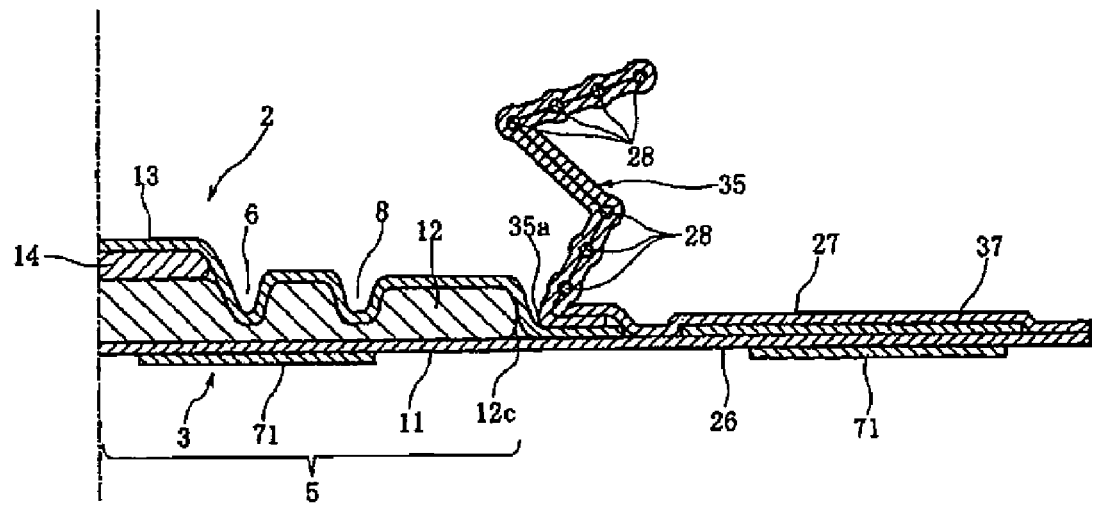
FIG. 2 is a sectional view taken along arrowed line II-II of FIG. 1.
Figure 3:
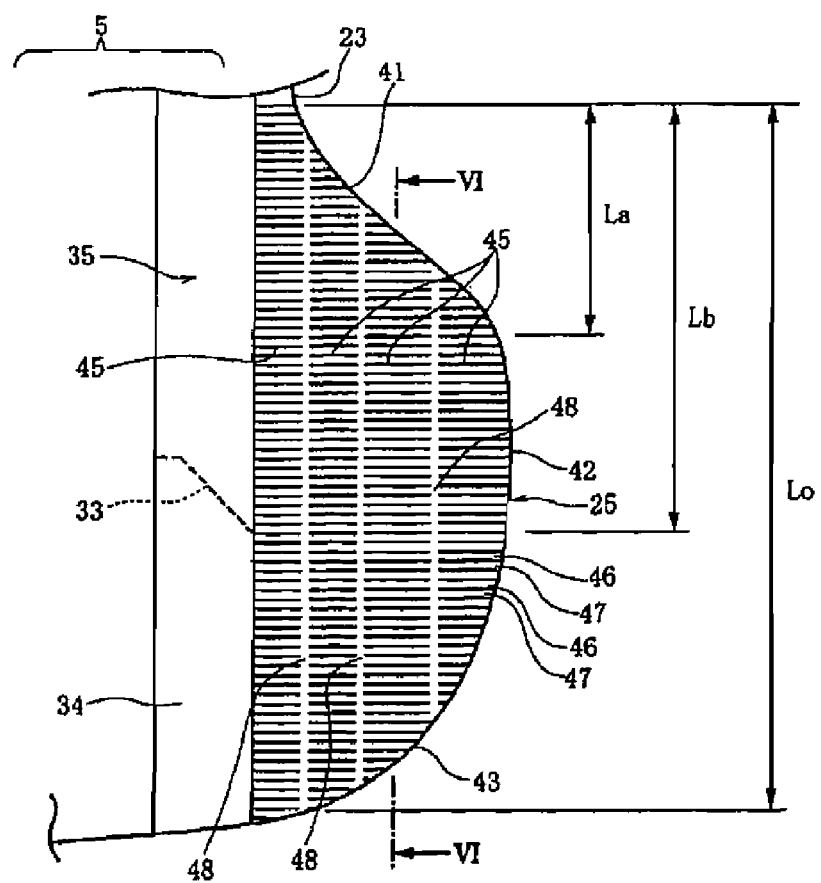
FIG. 3 is a fragmentary plan view showing a rear flap according to a first embodiment of the present invention.
Figure 4:
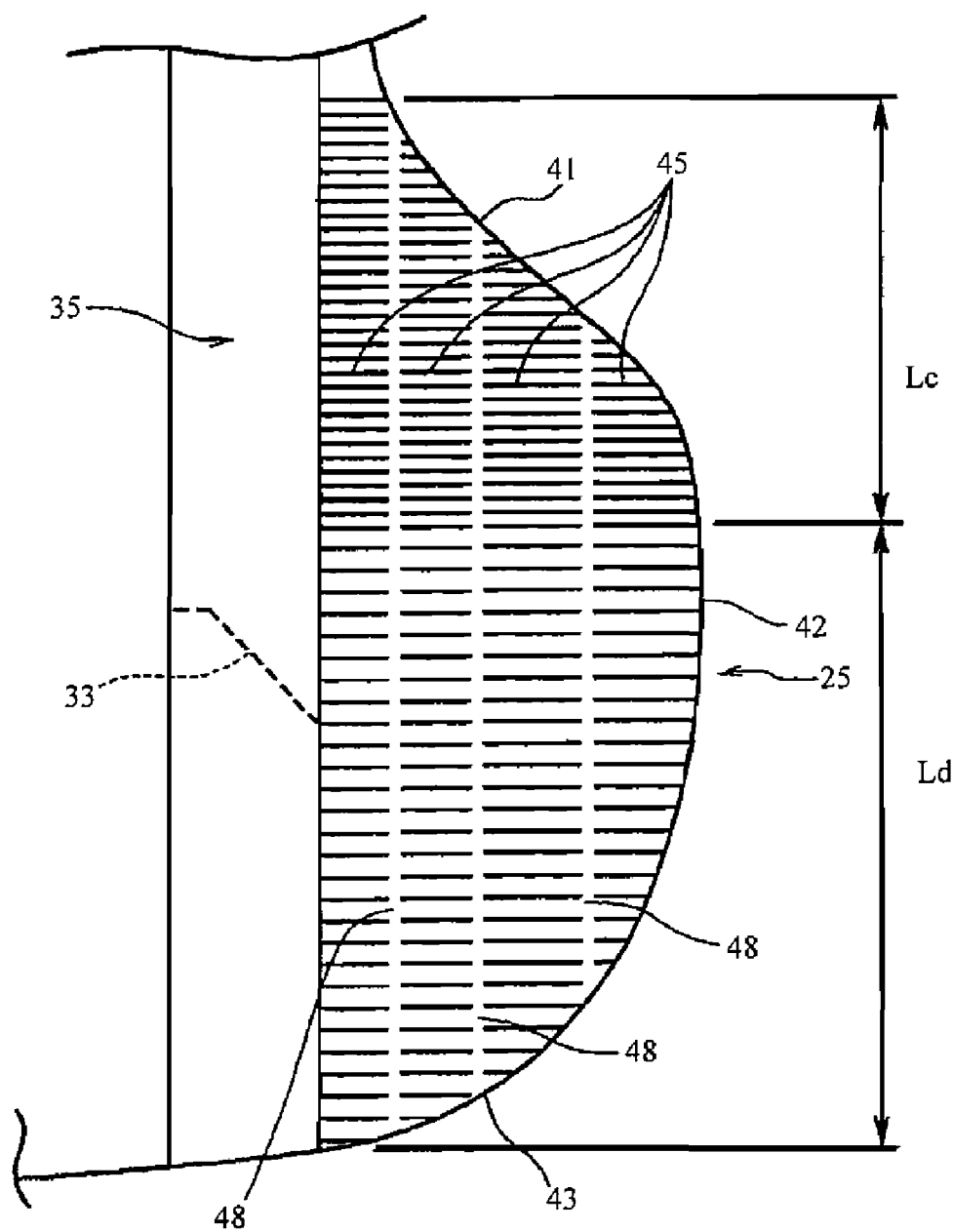
FIG. 4 is a fragmentary plan view showing a rear flap according to a second embodiment of the present invention.
Figure 5:
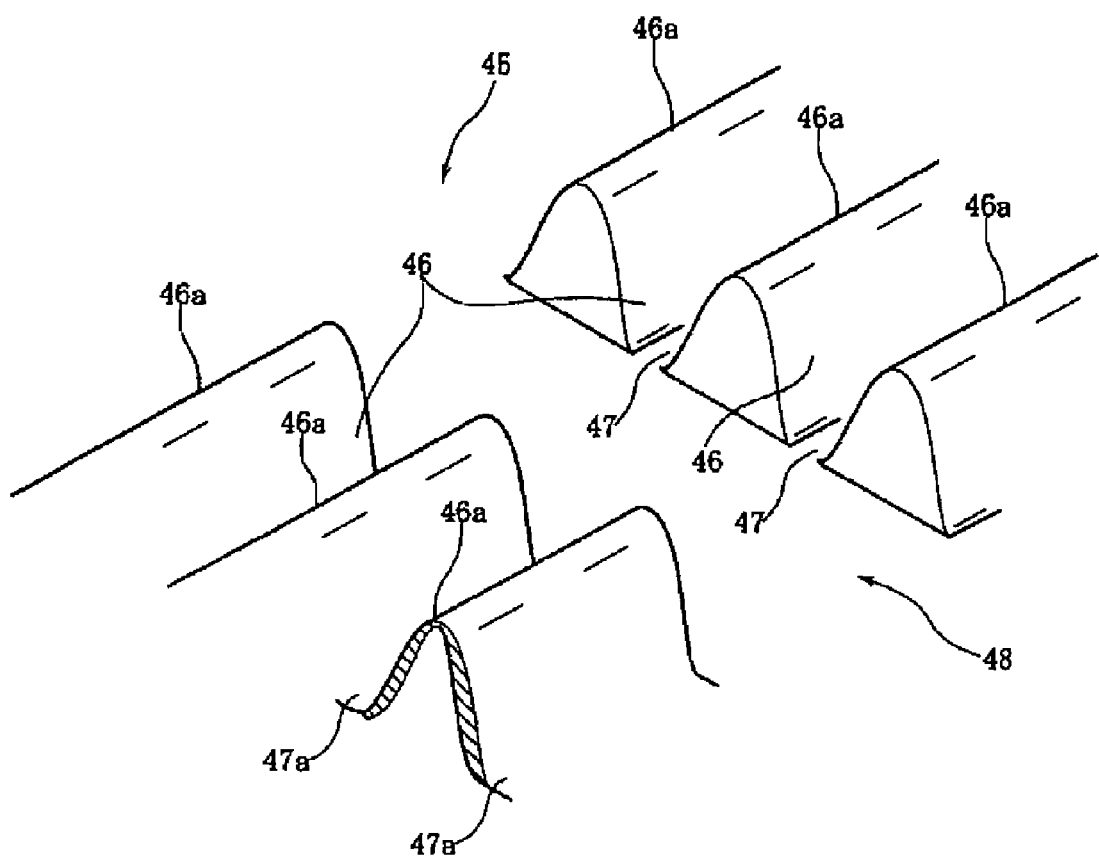
FIG. 5 is a partially sectional, enlarged perspective view of a portion of a rear flap according to one embodiment of the present invention.
Figure 6A:
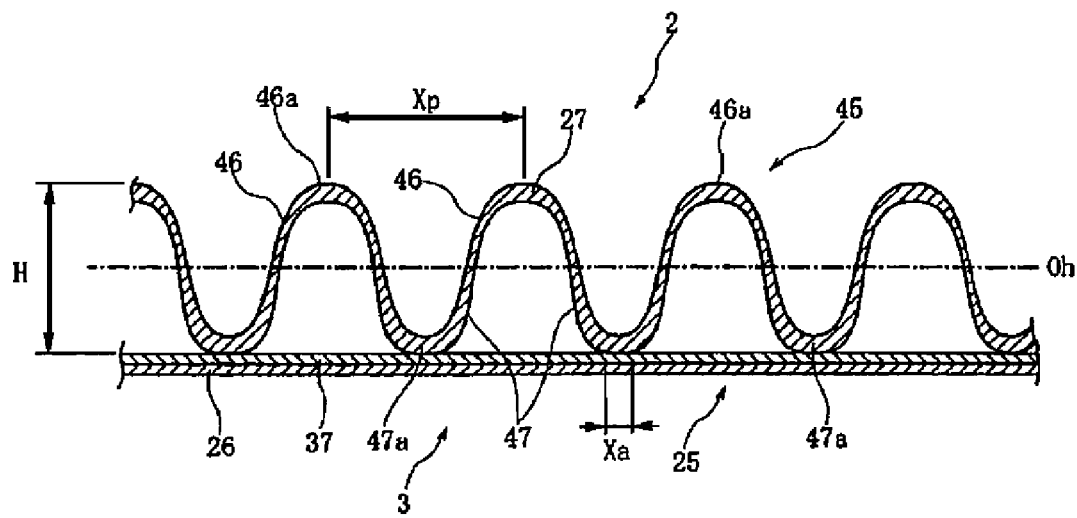
FIG. 6(A) is an enlarged sectional view taken along arrowed line VI-VI of FIG. 3
Figure 6B:
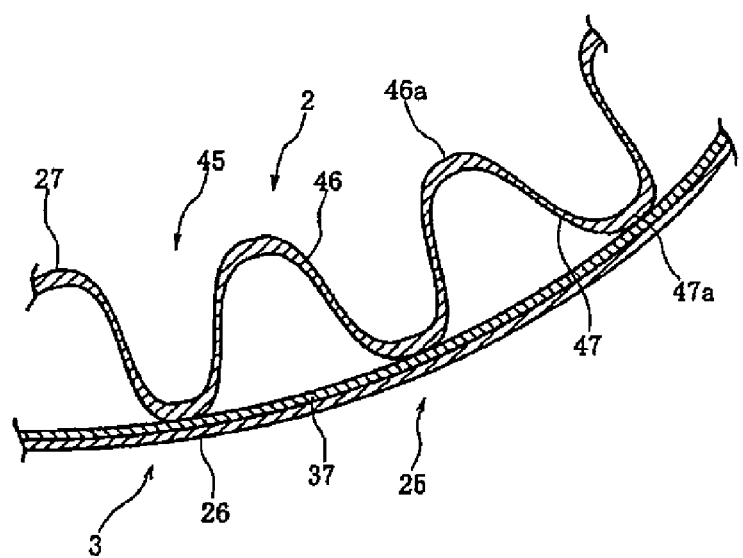
FIG. 6(B) is an enlarged sectional view showing a state where a rear flap is bent.
Figure 7:
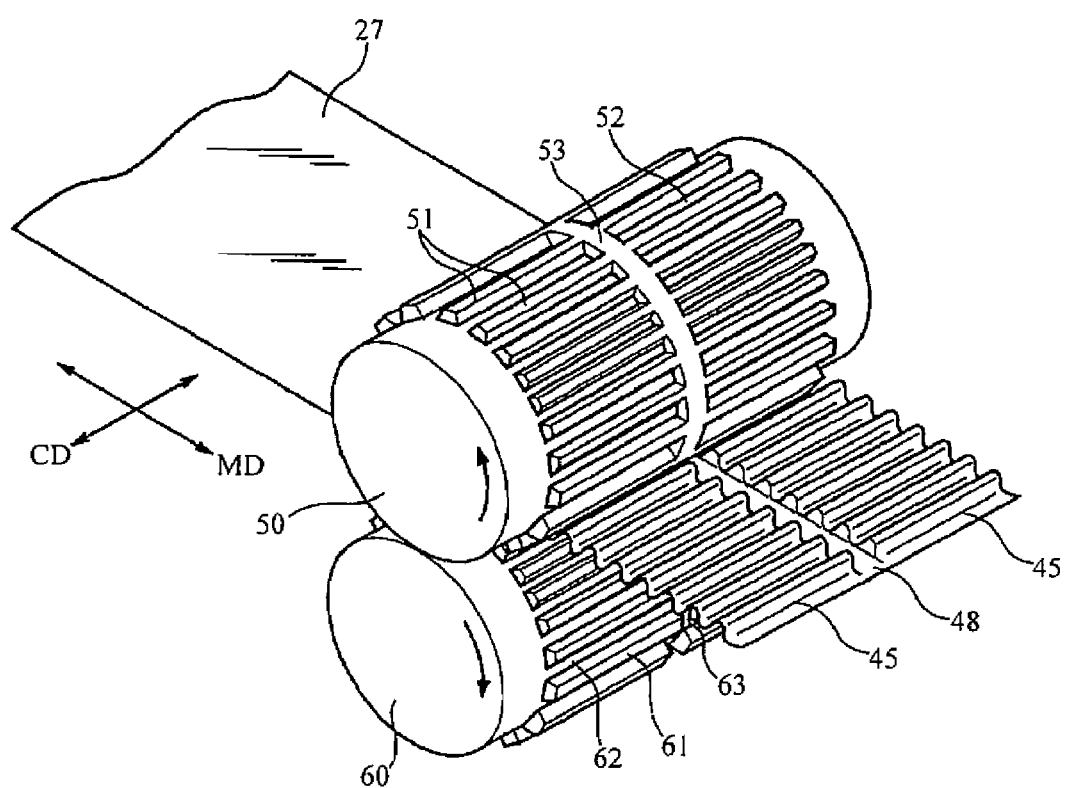
FIG. 7 is a perspective view showing a process of shaping corrugated regions and smooth regions.
Figure 9:
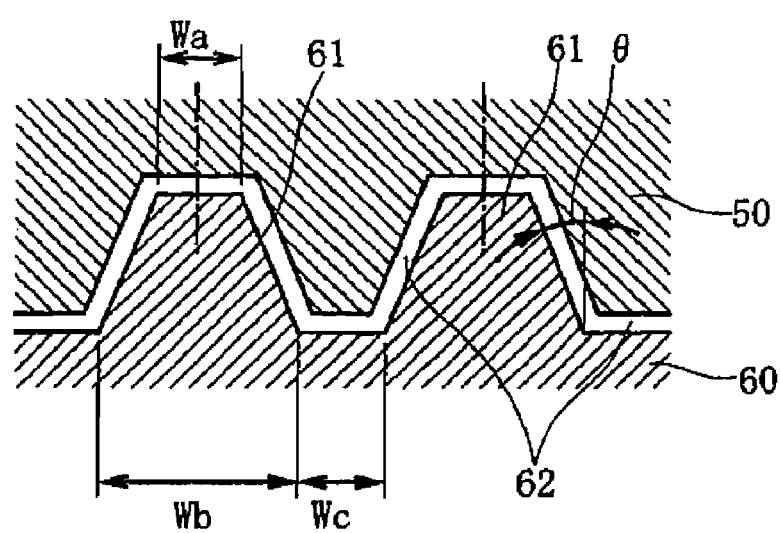
FIG. 9 is a sectional view showing the shape of projections and recesses of gear press rollers.

FIG. 1 is a plan view of a sanitary napkin according to one embodiment of the present invention; FIG. 2 is a sectional view taken along arrowed line II-II of FIG. 1; FIG. 3 is a fragmentary plan view showing a rear flap according to a first embodiment; FIG. 4 is a fragmentary plan view showing a rear flap according to a second embodiment; FIG. 5 is a partially sectional, enlarged perspective view of a portion of the rear flap; FIGS. 6(A) and 6(B) are enlarged sectional views taken along arrowed line VI-VI of FIG. 3; and FIGS. 7 and 9 are drawings for explaining a process of manufacturing a sheet for use in the rear flap.

FIGS. 1 and 2 show a sanitary napkin 1 which is elongated to have a larger dimension in a longitudinal direction than in a lateral direction and symmetrical about a longitudinal centerline Oy. The sanitary napkin 1 has longitudinally opposing front and rear edges 1a, 1b. When worn in the crotch region of a woman, the front edge 1a may be positioned on the pubis or the lower abdomen, while the rear edge 1b may be positioned near the intergluteal cleft (or the furrow of the buttocks) or the coccyx. Here, the intersection of the longitudinal centerline Oy and a lateral reference line Ox (see FIG. 1) may face the longitudinal center of the vaginal opening.

As shown in FIG. 2, the sanitary napkin 1 has a body surface 2 intended to face the wearer's body and a garment surface 3 intended to face an inner side of an undergarment. The sanitary napkin 1 is constructed of a liquid impermeable backsheet 11, a liquid absorbent layer 12 laid on the backsheet 11, and a liquid permeable topsheet 13 covering the liquid absorbent layer 12. As indicated by dotted line in FIG. 1, the liquid absorbent layer 12 may be of a longitudinally elongated generally rectangular shape with longitudinally opposing front and rear edges 12a, 12b and laterally opposing right and left edges 12c, 12d.

In the sanitary napkin 1, the portion enclosed by the front and rear edges 1a, 1b and the right and left edges 12c, 12d of the liquid absorbent layer 12 and their extensions is referred to as main body 5.

As shown in FIG. 1, the main body 5 may have a pair of longitudinal compressed lines 6, 6 where the body surface 2 is recessed by compressing the topsheet 13 and the liquid absorbent layer 12. The laterally spaced longitudinal compressed lines 6, 6 may be connected to each other by front and rear lateral compressed lines 6a, 6b. The area enclosed by the longitudinal compressed lines 6, 6 and the front and rear lateral compressed lines 6a, 6b is referred to as central absorbent area to which menstrual blood will be mainly applied. In the central absorbent area, as shown in FIG. 2, a bulky, liquid permeable cushion layer 14 may be disposed on the liquid absorbent layer 12 to have the body surface bulged toward the wearer's body.

The lateral distance between the longitudinal compressed lines 6, 6 may be the smallest on the lateral reference line Ox. In the vicinity of the lateral reference line Ox, front outside compressed lines 7, 7 may be provided outside the longitudinal compressed lines 6, 6, respectively. Behind the front outside compressed lines 7, 7, rear outside compressed lines 8, 8 may also be provided outside the longitudinal compressed lines 6, 6, respectively. Behind the rear lateral compressed line 6b, the rear outside compressed lines 8, 8 may be connected to each other by an outside lateral compressed line 8a.

In the embodiment shown in FIG. 1, three pairs of flaps project laterally in opposite directions from the main body 5. In the front part of the sanitary napkin 1, front flaps 21, 21 slightly project from the main body 5. In the vicinity of the lateral reference line Ox, fold-back flaps 22, 22 project from the main body 5. In the rear part of the sanitary napkin 1, rear flaps 25, 25 project from the main body 5. Between the fold-back flaps 22, 22 and the rear flaps 25, 25, indentations 23, 23 are formed to decrease the width of the sanitary napkin 1.

In the embodiment shown in FIG. 1, the front flaps 21, the fold-back flaps 22 and the rear flaps 25 have a second sheet 26 on the garment surface side and a first sheet 27 on the body surface side (see FIG. 2). The second sheet 26 may be a part of the backsheet 11 that is extended laterally from the main body 5. On the other hand, the first sheet 27 may be distinct from the topsheet 13. In the front flaps 21, the fold-back flaps 22 and the rear flaps 25, the first sheet 27 is laid on the second sheet 26 and partly joined to the topsheet 13.

As shown in FIG. 2, the first sheet 27 may be folded back upon itself to have a two-ply portion in which longitudinally extending elastic members 28 are fixed. The elastic members 28 are fixed to the first sheet 27 while being stretched longitudinally.

Forward and rearward of front and rear ends 31, 33 (see FIG. 1), the two-ply portion of the first sheet 27 is further folded back and bonded to the topsheet 13 to have front and rear fixation portions 32, 34. Between the front and rear ends 31, 33, most of the two-ply portion of the first sheet 27 remains free from the topsheet 13. When the body surface 2 is concavely curved with an elastic contractive force of the elastic members 28 acting between the front and rear ends 31, 33, the first sheet 27 rises up to form a leakage preventing wall 35 (see FIG. 2) between the front and rear ends 31, 33. The leakage preventing wall 35 has a lower end 35a on the topsheet 13.

In the fold-back flap 22, a rectangular reinforcing sheet 36 is interposed and bonded between the second sheet 26 and the first sheet 27. In the rear flap 25, another reinforcing sheet 37 is interposed and bonded between the second sheet 26 and the first sheet 27.

As shown in FIGS. 1 and 3, the rear flap 25 has a front part with a front edge 41, an intermediate part with an intermediate edge 42 and a rear part with a rear edge 43. In the front part, the width of the rear flap 25 gradually increases rearward; in the intermediate part, the width of the rear flap 25 is maximized and almost constant; and in the rear part, the width of the rear flap 25 gradually decreases rearward. When the sanitary napkin 1 is attached to the inner side of the crotch region of the undergarment and the lateral reference line Ox coincides with the center of the vaginal opening, the front edge 41 faces the wearer's thigh and extends along an edge of a leg opening of the undergarment.

According to a first embodiment shown in FIG. 3, the first sheet 27, which is a component of the rear flap 25, has corrugated regions 45. In the sectional view of FIG. 6, the rising height of the first sheet 27 in the corrugated region 45, as measured from the body surface of the reinforcing sheet 37, is indicated by H. In the corrugated region 45, the portions above a horizontal reference line Oh, which extends horizontally to bisect the height H, are hills 46, and the portions below the horizontal reference line Oh are valleys 47. The tops of the hills 46 are indicated by 46a and the bottoms of the valleys 47 are indicated by 47a.

As shown in FIG. 3, the corrugated regions 45 may extend the entire length L0 of the rear flap 25. The hills 46 and valleys 47 extend laterally and alternate with each other longitudinally. In the corrugated regions 45, the bottoms 47a of the valleys 47 are bonded to an underlying sheet but the rest of the first sheet 27 is unbonded thereto. In the embodiment shown in FIG. 6(A), the bottoms 47a of the valleys 47 are bonded to the reinforcing sheet 37. If the reinforcing sheet 37 is not provided in the rear flap 25, the bottoms 47a of the valleys 47 may be bonded to the second sheet 26.

Between the corrugated regions 45 of the rear flap 25, the first sheet 27 has a plurality of smooth regions 48 extending in a direction intersecting the hills 46 and valleys 47. In each smooth region 48, as shown in FIG. 5, the first sheet 27 may be flat or may have hills and valleys with a rising height that is smaller than the rising height H shown in FIG. 6(A). In other words, the smooth region 48 may be free of the hills 46 and valleys 47 or may have a smaller difference in level between hills and valleys than the corrugated region 45.

As shown in FIG. 3, each smooth region 48 may be strip-shpaed or linear and parallel to the longitudinal centerline Oy. Preferably, each smooth region 48 extends longitudinally (or without interruption). In the embodiment shown in FIG. 3., each rear flap 25 has three parallel smooth regions 48. Alternatively, the smooth region 48 may not extend the entire length of the rear flap 25. In this case, the smooth region 48 may extend longitudinally intermittently (i.e., may be composed of longitudinally spaced two or more sections of a given length). Longitudinally intermittent smooth regions 48a, 48b are shown for the rear flap 25 illustrated in FIG. 4.

The smooth regions 48 of the first sheet 27 may or may not be bonded to the reinforcing sheet 37.

In the corrugated region 45, as shown in FIG. 6(A), the hills 46 (or the valleys 47) may have a pitch Xp of about 0.5 to 5 mm and the height H may be about 0.5 to 5 mm. Moreover, the bottom 47a of the valley 47 may be bonded to the reinforcing sheet 37 for a width Wa of 0.1 to 3 mm. Here, the smooth regions 48 may have a width of about 0.1 to 3 mm.

Since the first sheet 27 has the corrugated regions 45 in the rear flap 25, the rear flap 25 is more flexible and has a lower bending stiffness than the front flap 21 and the fold-back flap 22.

More specifically, since the hills 46 and valleys 47 of the corrugated region 45 alternate with each other longitudinally and extend laterally in parallel to each other, as shown in FIG. 3, the longitudinal bending stiffness of the first sheet 27 can be significantly decreased. Furthermore, since the longitudinally-extending smooth regions 48 aid in bending, the lateral bending stiffness can also be decreased. Accordingly, the rear flaps 25 can easily deform to fit the wearer's body.

In the corrugated region 45, since the valleys 47 are bonded to the reinforcing sheet 37 or the second sheet 26 as shown in FIG. 6(A), the first sheet 27 is constricted from unfolding flat. Therefore, when a compressive force is exerted on the first sheet 27 in the corrugated region 45, the hills 46 can resist crushing, and when the compressive force is relieved, they can easily recover to their original shape.

When the rear flap 25 is bent as shown in FIG. 6(B), on the other hand, since the first sheet 27 can deform with the hills 46 approaching each other, the first sheet 27 is less resistant to bending. Therefore, when a bending force is exerted on the rear flap 25 as shown in FIG. 6(B), not only the first sheet 27 but also the second sheet 26 can follow the deformation with ease, which prevents folding of the second sheet 26. Hence, the rear flap 25 can be prevented from wrinkling or twisting.

Furthermore, since the hills 46 of the first sheet 27 are exposed externally on the body surface side of the rear flap 25, the substantial contact area of the rear flap 25 with the wearer's skin can be decreased to prevent the rear flap 25 from sticking to the wearer's skin.

In the first embodiment shown in FIG. 3, the corrugated regions 45 extend the entire length of the rear flap 25, while the front flap 21 and the fold-back flap 22 are free of the corrugated regions 45. Accordingly, the rear flap 25 has a lower stiffness than the front flap 21 and the fold-back flap 22.

Since the fold-back flap 22 is intended to be folded back along the side edges of the crotch region of the undergarment and adhered to the outer side of the undergarment for positioning of the sanitary napkin 1, it is not desirable to decrease stiffness. On the other hand, the rear flap 25 is intended to be kept in an unfolded state on the inner side of the undergarment. Accordingly, the rear flap 25 is made flexible and resilient as set forth above in order to follow the change in body shape and resist wrinkling and twisting. Furthermore, decreasing the stiffness of the rear flap 25 prevents causing an unpleasant feeling to the wearer's body.

Particularly when the sanitary napkin 1 is held between the thighs, the front part of the rear flap 25 may be deformed significantly and complicatedly. With the corrugated regions 45 and the smooth regions 48 formed in the front part of the rear flap 25, accordingly, the front part of the rear flap 25 can easily follow the change in body shape and the front edge 41 may not feel rigid when in contact with the thigh.

Hence, it is preferred that the corrugated regions 45 and the smooth regions 48 are formed at least in the front part of the rear flap 25. As set forth above, the front part of the rear flap 25 has the front edge 41 and refers to the area indicated by La in FIG. 3. In the embodiment shown in FIG. 1, moreover, the elastic members 28 exert an elastic contractive force between the front and rear ends 31, 33 to curve the main body 5 between the front and rear ends 31, 33. Therefore, it is preferred that the rear flap 25 has the corrugated regions 45 at least in the area forward of the rear end 33 (i.e., the area indicated by Lb in FIG. 3).

Figure 10:
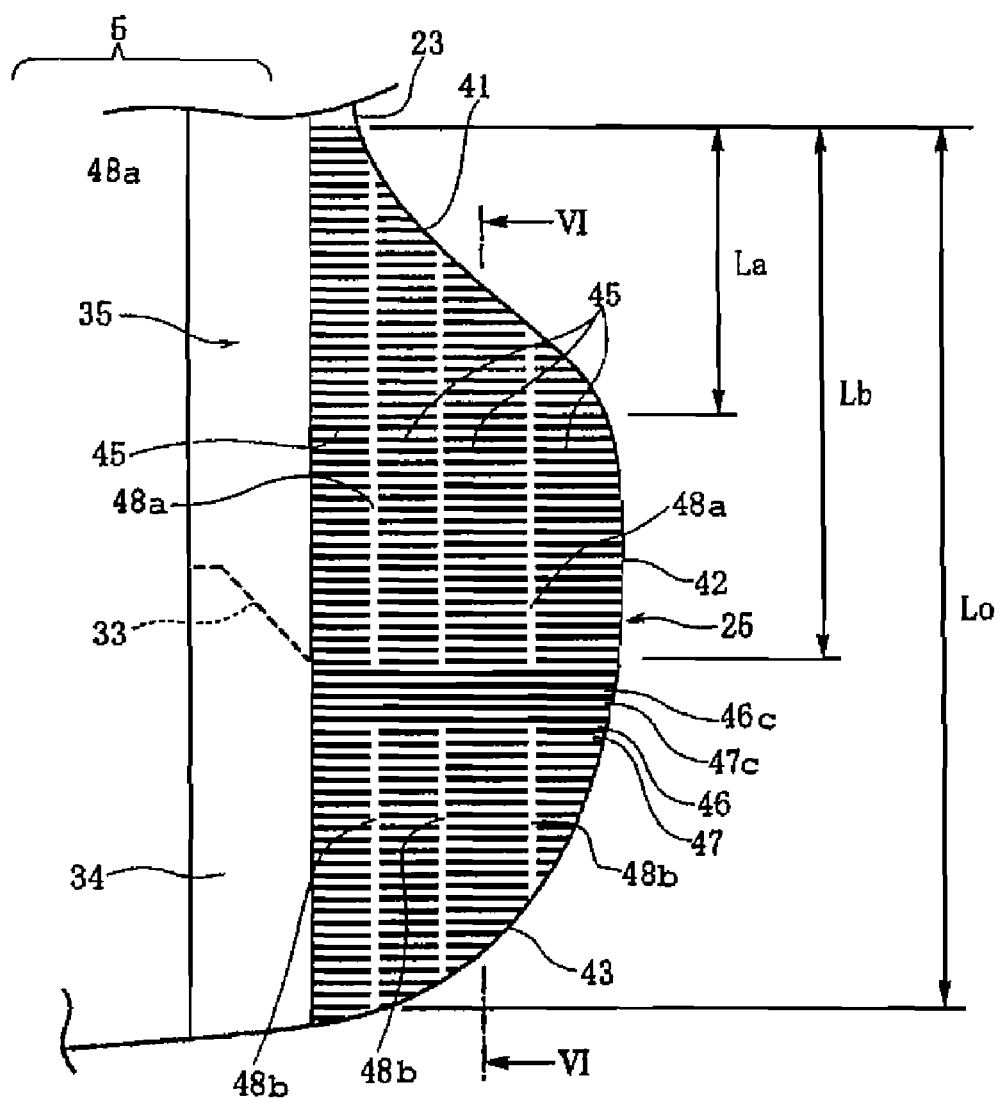
FIG. 10 is a fragmentary plan view showing a rear flap according to a third embodiment of the present invention.

Here, the intermediate part and the rear part of the rear flap 25 may be free of corrugated regions 45. In the second embodiment shown in FIG. 4, on the other hand, the hills 46 (or the valleys 47) may have a smaller pitch in a front area of a length Lc, which tends to receive a large deforming force when held between the thighs, than in a rear area of length Ld. In a third embodiment shown in FIG. 10, the parallel smooth regions 48a, 48b are spaced on either side of hills 46c and valleys 47c which are not segmented by smooth regions 48a, 48b.

In order to maintain bulk recovery properties, the first sheet 27 preferably comprises synthetic resin fibers. For example, there may be employed sheath/core bicomponent synthetic resin fibers, of which the core is polyester or polypropylene and the sheath is polyethylene, or side-by-side bicomponent synthetic resin fibers, of which one component is polyester or polypropylene and the other component is polyethylene. The first sheet 27 may be a through-air bonded, spunbonded or point-bonded nonwoven fabric of the above-mentioned synthetic resin fibers. The first sheet 27 may have a basis weight in the range of 10 to 40 g/m$^2$ and a thickness in the range of 0.1 to 1.5 mm.

FIG. 7 shows an apparatus for shaping two corrugated regions 45 and one smooth region 48 in the first sheet 27. The shaping apparatus has a first gear press roller 50 and a second gear press roller 60. The first gear press roller 50 has two rows of circumferentially-spaced-apart axial projections 51, axial recesses 52 defined between circumferentially adjacent axial projections 51, and a circumferential projection 53 continuous with the axial projections 51. The second gear press roller 60 has two rows of circumferentially-spaced-apart axial projections 61, axial recesses 62 defined between circumferentially adjacent axial projections 61, and a circumferential recess 63 defined between the two rows of the axial projections 61. The first and second gear press rollers 50, 60 mesh with each other such that the projections 51 fit in the recesses 62.

Accordingly, when the first sheet 27 is fed between the first and second gear press rollers 50, 60, the corrugated regions 45 may be formed with the hills and valleys alternating in a machine direction (MD). Here, the strip-shaped or linear smooth region 48 extends in the machine direction (MD). When manufacturing the rear flap 25 according to the embodiment shown in FIG. 3 or FIG. 4, the first gear press roller 50 may have three circumferential projections 53 and the second gear press roller 60 may have three circumferential recesses 63.

In the embodiments shown in FIGS. 3 and 4, the three smooth regions 48 extend parallel to the longitudinal centerline Oy, and therefore, the MD shown in FIG. 7 is parallel to the longitudinal centerline Oy of the sanitary napkin 1. And, when the first sheet 27 is fed out while the corrugated regions 45 are shaped with the first and second gear press rollers 50, 60 during the manufacturing process of the sanitary napkin 1, the smooth regions 48 extend parallel to the MD. Therefore, the first sheet 27 can be fed out along the longitudinal centerline Oy without meandering, which enables exact positioning of the corrugated regions 45 and the smooth regions 48 along the longitudinal direction of the sanitary napkin 1.

The corrugated region 45 thus manufactured has a relatively high fiber density in the tops 46a of the hills 46 and the bottoms 47a of the valleys 47, but the fiber density is decreased in the inclined portions between the tops 46a and the bottoms 47a, because fibers constituting the nonwoven fabric are stretched by the projections of the gear press rollers. Accordingly, the stiffness of the first sheet 27 after formation of the corrugated regions 45 is lower than that before formation of the corrugated regions 45.

The first sheet 27 after formation of the corrugated regions 45 has a ring crush strength preferably equal to or less than 60%, more preferably equal to or less than 50%, of an original ring crush strength as measured before formation of the corrugated regions 45.

The ring crush strength may be measured as follows. A strip (100 mm in the MD and 20 mm in a cross direction (CD) perpendicular to the MD) is cut out of the first sheet used for the embodiments shown in FIGS. 3 and 4 and then rolled into a 20 mm height cylinder with longitudinally opposing ends laid one on the other to have a 2 mm overlap and stapled together. This cylinder is set on an autograph compression tester manufactured by Shimadzu Corporation and diametrically compressed at a measuring speed of 10 mm/min with a load up to 50 N. The measured maximum load is taken as a ring crush strength.

On the other hand, when the first sheet 27 is bonded to the underlying sheet, as shown in FIG. 6(A), the corrugated region 45 preferably has a bulk recovery ratio in the range of 70% to 90%.

The bulk recovery ratio may be measured as follows. A sample (20 mm in both the MD and the CD) is cut out of the rear flap 25 and a thickness Ta under pressure of 49 Pa is measured using a microscope manufactured by Keyence Corporation. Then, pressure of 14.7 kPa is applied thereto for 3 hours and after the sample is allowed to stand for 5 minutes subsequent to removal of the pressure, a thickness Tb is measured using the same microscope. The bulk recovery ratio is expressed by (Tb/Ta)×100 (%).

On the body surface side of the rear flap 25, the corrugated region 45 preferably has a plane contact ratio in the range of 10% to 40%.

Figure 8:
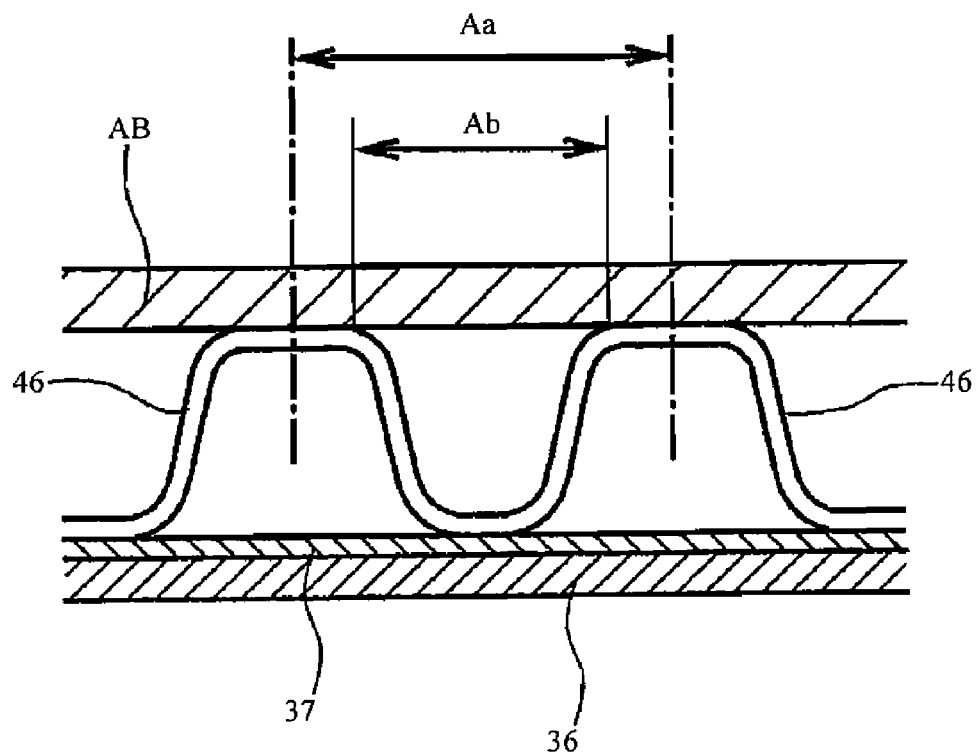
FIG. 8 is a sectional view showing a method for measuring a plane contact ratio.

The plane contact ratio may be measured as follows. A sample (20 mm in both the MD and the CD) is cut out of the rear flap 25 and then pressed for 5 minutes under pressure of 14.7 kPa with an acrylic board AB put on the tops of the hills 46, as shown in FIG. 8. When the pressure is removed, a pitch Aa (i.e., a center-to-center distance between adjacent hills) and a distance Ab between adjacent contact areas, where the hills are in contact with the acrylic board AB, are measured using a microscope manufactured by Keyence Corporation. The plane contact ratio is expressed by (Aa−Ab)/Aa×100 (%).

If the ring crush strength, the bulk recovery ratio and the plane contact ration are in the foregoing ranges, the rear flaps 25, which are kept in an unfolded state on the inner side of the undergarment for coming into close contact with the wearer's body, can easily deform in accordance with the wearer's body shape, while resisting wrinkling and twisting and also preventing causing an unpleasant feeling.

The following examples of the first sheet 27 were actually manufactured and tested for the above-mentioned properties.

As Example 1, a spunbonded nonwoven fabric was made of sheath/core polyethylene/polypropylene bicomponent fibers to have a basis weight of 22 g/m² and then processed with the gear press rollers 50, 60 to have corrugated regions 45, as shown in FIG. 9. Between adjacent corrugated region 45, 1 mm width smooth regions 48 were defined to extend continuously in the MD. The smooth regions 48 were spaced 10 mm apart in the CD. In the gear press rollers 50, 60 shown in FIG. 9, Wa was 0.3 mm, Wb was 0.7 mm, Wc was 1.36 mm, and the angle θ of the inclined surface of each gear tooth was 23.434 degrees. The corrugated regions 45, as well as the smooth regions 48, were formed at a rate of 10 mm/min through the gear press rollers 50, 60. The obtained sheet had a ring crush strength of 0.07442 N. This was 49.7% of 0.1496 N, which was an original ring crush strength as measured before formation of the corrugated regions 45 and the smooth region 48.

As Example 2, a through-air bonded nonwoven fabric was made of sheath/core polyethylene/polyester bicomponent fibers to have a basis weight of 20 g/m² and then processed with the gear press rollers 50, 60 to have the corrugated regions 45 and the smooth regions 48 in the same manner as Example 1. The obtained sheet had a ring crush strength of 0.033 N. This was 35.3% of 0.0936 N, which was an original ring crush strength as measured before formation of the corrugated regions 45 and the smooth region 48.

Examples 1 and 2 were each bonded to a polyethylene resin sheet having a basis weight of 23.5 g/m² to obtain samples having the same construction as the rear flap 25. The sample with Example 1 had a bulk recovery ratio of 95% and the sample with Example 2 had a bulk recovery ratio of 97%. Both the samples had a plane contact ratio in the range of 22 to 27%.

The second sheet 26 (or the backsheet 11) may be a polyethylene resin sheet having a basis weight in the range of about 15 to 45 g/m². Alternatively, the second sheet 26 may be a nonwoven fabric.

The reinforcing sheet 37 is provided to reinforce the second sheet 26 and also prevent the pitch of the valleys 47 from decreasing or increasing when the corrugated region 45 of FIG. 6(A) is subjected to a crushing force for maintaining the bulk recovery ratio. Moreover, when the rear flap 25 is bent as shown in FIG. 6(B), the reinforcing sheet 37 can exert a force to restore the rear flap 25 to its original flat state as shown in FIG. 6(A).

The reinforcing sheet 37 may be made of mere paper or nonwoven fabric, but a resilient sheet, such as a urethane foam sheet, a polyethylene foam sheet, a synthetic rubber sheet or a stretchable nonwoven fabric, is preferably used.

The other components of the sanitary napkin 1 may be similar to those of the conventional sanitary napkin. The liquid absorbent layer 12 may be made of pulp and super-absorbent polymer (SAP). The topsheet 13 may be a liquid-permeable nonwoven fabric or an apertured film with liquid passage apertures. The cushion layer 14 may be a through-air bonded nonwoven fabric.

On the garment surface 3 of the sanitary napkin 1, as shown in FIG. 2, the main body 5, the fold-back flaps 22 and the rear flaps 25 may have pressure-sensitive adhesive layers 71.

The sanitary napkin 1 may be worn such that the main body 5 is fixed on the inner side of the crotch region of the undergarment through the pressure-sensitive adhesive layers 71, the fold-back flaps 22 are folded back along the side edges of the crotch region of the undergarment and fixed on the outer side of the undergarment through the pressure-sensitive adhesive layers 71, and the rear flaps 25 are fixed in an unfolded state on the inner side of the undergarment through the pressure-sensitive adhesive layers 71. Here, the front edge 41 of the rear flap 25 may extend along the edge of the leg opening of the undergarment and faces the wearer's thigh.

As has been described above, the rear flaps 25, which are allowed to flexibly bend in both the longitudinal and lateral directions, can follow the movement of the wearer's body and hardly gives an unpleasant feeling to the wearer's body, particularly to the thighs. In addition, since the rear flaps 25 are resilient to compression and bending, they are resistant to wrinkling and twisting. Furthermore, since the rear flaps 25 decrease the contact area against the wearer's skin, they hardly stick to the wearer's skin.

Although the present invention has been illustrated and described with respect to exemplary embodiments thereof, it should be understood by those skilled in the art that the foregoing and various other changes, omission and additions may be made therein and thereto, without departing from the spirit and scope of the present invention. For example, the hills 46 and valleys 47 may be inclined at 45 degrees or less to a direction perpendicular to the longitudinal centerline Oy, if desired. In addition, or alternatively, the smooth regions 48 may be inclined at 10 degrees or less to the longitudinal centerline Oy, if desired.

Therefore, the present invention should not be understood as limited to the specific embodiments set out above but to include all possible embodiments which can be embodied within a scope encompassed and equivalent thereof with respect to the feature set out in the appended claims.

What is claimed is:

1. A sanitary napkin comprising:
an elongated main body having a liquid absorbent layer for absorbing and retaining liquid, the elongated main body being symmetrically disposed about a longitudinal centerline extending in an elongated direction of the elongated main body; and
rear flaps located in proximity to a rear edge of the sanitary napkin, and projecting laterally in opposite directions from laterally opposing side edges of the liquid absorbent layer, the sanitary napkin being adapted to be worn with the rear flaps kept in an unfolded state on an inner side of an undergarment,
each rear flap including a first sheet which is corrugated such that each rear flap has adjacent corrugated regions and at least one strip-shaped or linear smooth region extending continuously over a substantially entire length of each rear flap between the adjacent corrugated regions and in a direction that is substantially parallel to said longitudinal centerline, each corrugated region having hills and valleys which extend laterally and alternate with each other in a direction that is substantially parallel to said longitudinal centerline, the smooth region being free of the hills and valleys or having a smaller difference in level between hills and valleys than the corrugated region.

2. The sanitary napkin of claim 1, wherein each rear flap further includes a second sheet laid on a garment surface of the first sheet, wherein the corrugated regions are bonded at bottoms of the valleys to the second sheet or another sheet disposed between the first sheet and the second sheet.

3. The sanitary napkin of claim 1, where the hills and valleys of the corrugated region are arranged at a fixed pitch.

4. The sanitary napkin of claim 1 where the hills and valleys of the corrugated region are arranged at a finer pitch in a front part of each rear flap than in a rear part behind the front part.

5. The sanitary napkin of claim 1, wherein each rear flap has a plurality of smooth regions at laterally spaced intervals.

6. The sanitary napkin of claim 5, wherein the corrugated regions of each rear flap decrease a longitudinal bending stiffness of the first sheet of the rear flap and the laterally spaced smooth regions of each rear flap decrease a lateral bending stiffness of the rear flap, thereby enabling each rear flap to bend longitudinally and laterally for conforming to a body shape of a wearer.

7. The sanitary napkin of claim 1, wherein the corrugated region has a bulk recovery ratio in the range of 70% to 90%.

8. The sanitary napkin of claim 1, wherein the first sheet has a ring crush strength equal to or less than 60% of an original ring crush strength as measured before formation of the corrugated regions and the smooth region.

9. The sanitary napkin of claim 1, further comprising fold-back flaps located forward of the rear flaps in a direction along said centerline and in proximity to a lateral reference line, wherein:
the intersection of said centerline and said lateral reference line define a vaginal positioning point, and
the sanitary napkin is adapted to be worn with the fold-back flaps positioned in a folded state on an outer side of the undergarment.

10. The sanitary napkin of claim 1, wherein the adjacent corrugated regions and the at least one strip-shaped or linear smooth regions between adjacent corrugated regions substantially cover an entire area of each rear flap.

* * * * *